United States Patent [19]
Bazell et al.

[11] 3,930,580
[45] Jan. 6, 1976

[54] STERILIZABLE, PEELABLE POUCH OR TRAY ASSEMBLY

[75] Inventors: Seymour Bazell, Skokie; Edward M. Goldberg, Glencoe, both of Ill.

[73] Assignee: Medical Products Corporation, Skokie, Ill.

[22] Filed: Oct. 19, 1973

[21] Appl. No.: 407,890

[52] U.S. Cl. .............. 206/439; 206/364; 206/498; 229/48 T; 229/51 TS; 229/66
[51] Int. Cl.² ........................................ A61B 19/02
[58] Field of Search .......... 206/305, 364, 439, 498; 229/51 TS, 48 T, 55, 66

[56] References Cited
UNITED STATES PATENTS

| 3,093,242 | 6/1963 | Huyck et al. | 206/364 |
|---|---|---|---|
| 3,186,628 | 6/1965 | Rohde | 206/364 |
| 3,291,374 | 12/1966 | Lepisto et al. | 229/55 |
| 3,322,603 | 7/1967 | Kamins et al. | 229/55 |
| 3,556,318 | 1/1971 | Hollis | 229/55 |
| 3,604,616 | 9/1971 | Grief | 229/55 |
| 3,687,352 | 8/1972 | Kalajian | 229/48 T |
| 3,761,013 | 9/1973 | Schuster | 206/439 |

Primary Examiner—George E. Lowrance
Assistant Examiner—Bruce H. Bernstein
Attorney, Agent, or Firm—Molinare, Allegretti, Newitt & Witcoff

[57] ABSTRACT

A sterilizable, peelable pouch or tray for medical and surgical equipment. The pouch comprises two superimposed sheets, preferably of autoclavable plastic, interconnected by an edge-strip of folded-over plastic affixed to the exterior surfaces of the sheet. The strip extends around at least a portion of the perimeter of the sheet edges and serves to provide a readily separable interconnection between the sheets. The sheets are separated by merely peeling one sheet back, thereby ripping the folded-over strip at the juncture between the two sheets. The tray assembly is similar with an upper plastic sheet removably, peelably affixed to a lower formed plastic cardboard or metal tray by the perimeter strips.

11 Claims, 6 Drawing Figures

U.S. Patent   Jan. 6, 1976   3,930,580
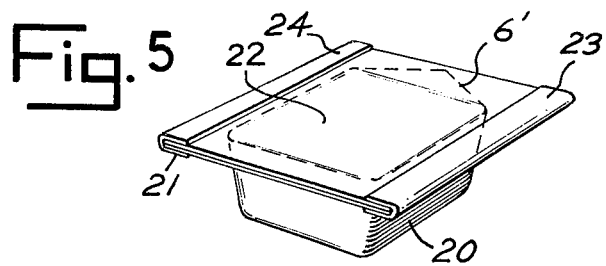
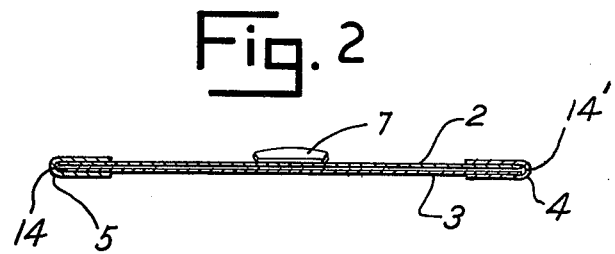
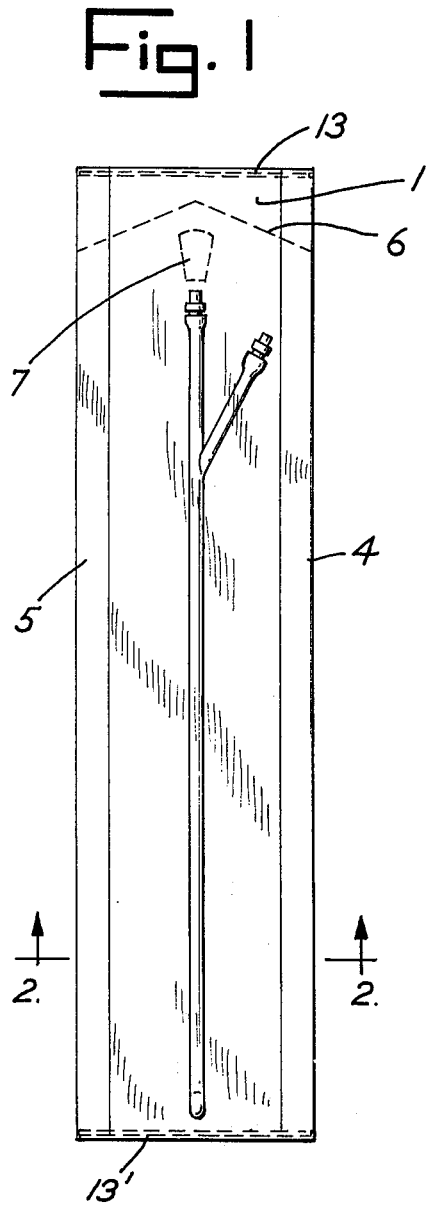
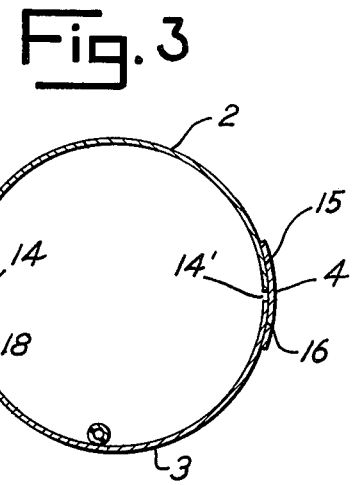
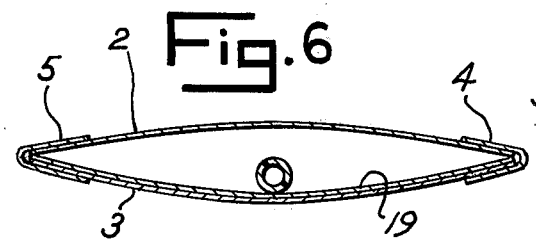
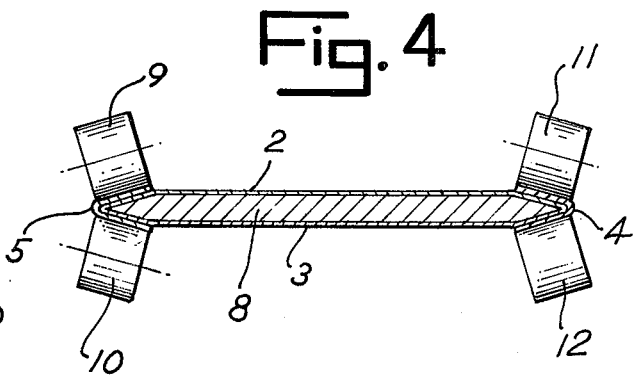

STERILIZABLE, PEELABLE POUCH OR TRAY ASSEMBLY

BACKGROUND OF THE INVENTION

This invention pertains to pouches and trays, particularly pouches or trays for medical and surgical equipment which must be sterilized before use.

In hospitals, clinics and doctors' offices, pouch-contained surgical instruments are sterilized by placing the pouch containing the desired piece of equipment, e.g., catheters, suture sets, etc., in an autoclave. The instruments or equipment can then be handed, after sterilization in the autoclave, to the user in a sterile condition in the pouch. The pouch is then ripped open and the desired instrument removed.

The sterilization pouches that are commonly used now comprise a sheet of transparent plastic bonded on its edges to a paper sheet. Instruments are removed by peeling the plastic sheet away from the paper sheet. Transparency is desirable since this allows easy identification of the desired instrument contained in the pouch.

One of the problems with these prior art pouches is that they cannot consistently withstand the rigors of autoclaving. For example, the paper is adversely affected by excessive humidity and moisture droplets. This leads to rupture of the pouch as it expands in the autoclave, or separation of the paper and plastic sheets. Further, the paper generates loose fibers and pulp when the plastic sheet is removed. This frequently results in instrument and surgical site contamination, leading to retarded healing, infection, and the like.

Further, incomplete separation, or separation along lines other than those intended, causes instruments to get hung up in the present-day pouches. The instruments must then be handed to remove them from the pouch. This may delay in-progress operations or result in impairing the sterility of the instrument.

SUMMARY OF THE INVENTION

It is an object of this invention to provide a sterilizable pouch or tray that can withstand the rigors of sterilization in an autoclave.

It is another object of the invention to provide a sterilizable pouch or tray that eliminates the presence of loose fibers and pulp when opened and does not present non-sterile edges or areas to its contents.

It is another object of this invention to provide a sterilizable pouch of tray that peels open easily after sterilization in an autoclave.

It is another object of this invention to provide a sterilizable pouch or tray that will not transmit water as a liquid but will allow the transmission of steam or other sterilizing vapor.

It is another object of this invention to provide a sterilizable pouch or tray that is strong enough to resist rupture during autoclaving.

It is another object of this invention to provide a sterilizable pouch that can be inexpensively manufactured as a continuous tube.

Still other objects will be evident from the description which follows.

In an embodiment of this invention, therefore, there is provided a sterilizable, peelable pouch or tray assembly for medical and surgical equipment. The pouch embodiment of this invention comprises two superimposed plastic sheets interconnected by a continuous plastic strip folded over and attached to the exterior surfaces of the superimposed sheets at the edges thereof. This folded-over strip extends around at least a portion of the perimeter of the sheet edges. Any remaining, unclosed portions are sealed together such as by heat sealing the sheets together to form an enclosed pouch. The folded-over perimetric edge strips define a readily separable interconnection between the sheets wherein the strips are readily ripped apart at the interconnnection of the two sheets when one of the sheets is peeled back. The plastic sheets are preferably of sufficient strength to withstand the temperatures and pressures encountered in an autoclave and should not transmit liquid water. The sheets may, however, transmit sterilizing vapor, e.g. steam, ethylene oxide and the like.

In a preferred embodiment the sheets are elongated, generally rectangular sheets wherein a pair of strips are positioned over and attached to the side edges of the sheets. The ends are then heat-sealed to provide an enclosed pouch.

Relability of the pouch can be enhanced by providing an appropriately placed scoring on the exterior of one of the sheets whereby an initial peel point can be established. Preferably, a free tab is positioned adjacent to the score to provide a surface to pull and start the peel.

The tray embodiment of this invention comprises an upper plastic sheet superimposed over the top of a formed surgical tray wherein the plastic sheet is bonded to the tray by the perimeter strips as set forth in the pouch embodiment.

Other objects and embodiments may be found in the following, more detailed description of the invention.

BRIEF DESCRIPTION OF THE DRAWINGS

FIG. 1 is a plan view of a preferred embodiment of a peelable pouch according to this invention showing a catheter therein;

FIG. 2 is a detailed, cross-sectional end view taken along section line 2—2 of FIG. 1, upon removal of the catheter, illustrating the interconnection of the face sheets and the folded-over side strips;

FIG. 3 is a cross-sectional end view as in FIG. 2 illustrating the pouch when expanded due to pressure differentials that develop during autoclaving;

FIG. 4 is a schematic diagram illustrating a preferred method of manufacturing the peelable pouch illustrated in FIG. 1;

FIG. 5 is a perspective view of a tray manufactured according to the present invention; and FIG. 6 is a cross-sectional view of a pouch as illustrated in FIG. 1 showing a catheter therein and an inner paper lining.

DETAILED DESCRIPTION OF THE INVENTION

Referring first to FIGS. 1 and 2, there is illustrated a sterilizable, peelable pouch 1 according to a preferred embodiment of this invention. Pouch 1 comprises a top sheet 2 and a bottom sheet 3 interconnected by folded-over side edge strips 4 and 5. Preferably, side strips 4 and 5 are heat-sealed to the exterior surfaces of top sheet 2 and bottom sheet 3. Both ends of pouch 1 are heat-sealed shut at 13, 13' to provide a closed pouch.

As more clearly illustrated in FIG. 2, side edge strips 4 and 5 are elongated strips of plastic, preferably of the same composition as sheets 2 and 3, that are folded over 180° at approximately the center of the strip. These strips are characterized as having strength under tension but which can be torn by shear. When sheets 2 and 3 are placed in the fold of strips 4 and 5 and sealed thereto, there is formed peel zones or strips 14, 14' defined by a single thickness of plastic. When top sheet 2 is peeled back, sheet 2 separates from bottom sheet 3 by tearing the single thickness of plastic along peel zone 14. This results in a uniform removal of one sheet from the other without the exposure of unsterilized edges, etc., to the contents of the pouch. The pouch is peeled back strictly along the area defined by peel zones 14, 14' because of the double thickness of plastic (the edge strip laminated to top and/or bottom sheets) on either side of zones 14, 14'.

A score or series of scores 6 can be placed diagonally with respect to the juncture of the top and bottom sheets near one end of pouch 1 to facilitate opening. These scores provide an access area that allows a user to start the peel. This score can be formed by means well known to those trained in the art such as embossing or partial cutting (scoring) with a suitable press. In an alternative embodiment, score 6' can be positioned diagonally across one of the corners of the pouch (see FIG. 5). In this embodiment, a corner can be simply torn off and the top sheet peeled back. In any event, tab 7, heat-sealed to top sheet 2 adjacent to score 6, provides a convenient method for starting the peel. By pulling tab 7, top sheet 2 is separated at score 6 can be peeled from bottom sheet 3 along peel zone 14.

A distinct advantage of the present invention is that pouch 1 is strong enough to resist blowouts or rupture during autoclaving. In a typical autoclave sterilization operation, the pouch is placed in the autoclave and the inner, pressure chamber is allowed to reach a temperature of at least 250°F. with a steam pressure of about 15–17 psig. After about 30 minutes, the pressure in the pressure chamber is suddenly relieved and all of the steam pressure, which has by now permeated pouch 1 because of its porosity, is retained in the bag, thereby causing the bag to expand as illustrated in FIG. 3. This expansion occurs particularly in autoclaves that go through a drying cycle wherein the pressure in the pressure chamber drops to about 23–27 inches of mercury.

The prior art pouches frequently break because of the pressure developed in the pouch during the autoclaving cycle. This is not a problem with the pouches or trays of the present invention. Referring to FIG. 3, when the pouches of the present invention are inflated, they distend like a balloon. When so inflated, peel zones 14 and 14' in edge strips 4 and 5 are under pure tension and will not tear or separate. The heat-sealed interconnections 15, 16, 17 and 18 of strips 4 and 5 are under shear stresses and are of sufficient strength to prevent sheets 2 and 3 from separating from each other. Further, scores 6 are also under primarily tension forces and will not lead to rupture of the pouch. However, peel zones 14 and 14', when sheet 2 is pulled back, are placed under shear forces which readily allow the single plastic thickness to tear open along zones 14 and 14' with minimum effort.

Pouch 1 should be manufactured from a plastic material that will not allow a liquid such as water to pass therethrough. Preferably, however, at least one of the sheets is manufactured from a plastic that is capable of passing a sterilizable vapor, e.g. steam under pressure, ethylene oxide or the like. Although at least one of the sheets is preferably transparent to allow a user to ascertain the contents of the pouch, as seen in FIG. 6, the interior faces of one of the sheets can be laminated with a sheet of paper 19 for reinforcement or to provide a printable surface or the like. Since the side strips are laminated to the exterior of the pouch and are not in contact with the paper when the pouch is peeled open, no loose fibers, etc., will be formed that can contact the enclosed instrument.

Plastics which possess the enumerated properties are well known to those trained in the art and include polyolefins, such as ethylene and propylene, polyaromatics, such as styrenes, polyvinylhalides, such as polyvinylchlorides, etc. A preferred plastic is spun nylon or spun polypropylene since it is stable under the temperatures encountered in an autoclave. A spun polyethylene such as TYVEK sold by duPont can also be used but it is not as good a material for use in an autoclave as spun nylon.

A pouch as illustrated in FIG. 1 can be quickly and inexpensively manufactured according to the process schematically illustrated in FIG. 4. According to this process, top sheet 2 and bottom sheet 3 are spaced on either side of a spacer 8, such as Teflon-coated steel or the like. Side strips 4 and 5 are folded over the edges of sheets 2 and 3 and are then heat-sealed together by the action of heated contact pressure rollers 9, 10, 11 and 12 as these rollers heat and press the sheets and strips together. This produces a continuous "tube" that can be subsequently cut into desired lengths and heat-sealed to produce the pouch.

Illustrated in FIG. 5 is a tray 20 covered with a plastic sheet 22 according to a further embodiment of this invention. Tray 20 has a flat substantially horizontal edge 21 extending around the perimeter of the top of tray 20. Sheet 22 is connected to the side edges of tray 20 by folded over side strips 23 and 24 which are suitably bonded to the top of sheet 20 and the bottom of edge 21 in a manner similar to the pouch embodiment illustrated in FIG. 1, etc. The front and back edges of sheet 22 are sealed directly to edge 21 to provide a complete seal for the tray. A score 6' diagonally positioned across a corner of sheet 22 facilitates removal of sheet 22 in the same manner as described in relationship to the pouch embodiment. Similarly, side strips 23 and 24 can be attached to tray 20 and sheet 22 in the manner shown in FIG. 4 for the pouch by passing the folded over side strips and edges through an opposed heated roller assembly.

It should be understood that various modifications within the scope of this invention can be made by one of ordinary skill in the art without departing from the spirit thereof. I, therefore, wish my invention to be defined by the scope of the appended claims as broadly as the prior art will permit, and in view of this specification if need be.

We claim:

1. A sterilizable, peelable, medical and surgical equipment-containing assembly which comprises:
 a bottom member;
 a plastic face sheet superimposed over the bottom member;
 a continuous plastic strip folded over and sealed to the exterior surfaces of the bottom member and the plastic sheet on at least a portion of the perimetric edges of said sheet and said member to define a readily separable interconnection between the sheets separable solely at the juncture of the bottom member and the plastic face sheet, said strip having the properties of strength under tension and partability under shear;

means for initiating peeling of said face sheet from said bottom member solely at said juncture, positioned diagonally to the juncture of the top sheet and the bottom member; and means for sealing the remaining perimeter of the sheets, said plastic sheet comprising a plastic that is resistant to transmission of liquid water, wherein the plastic sheet is separated from the first member by peeling said sheet from said member.

2. An assembly as in claim 1 wherein said bottom member is a plastic sheet.

3. An assembly according to claim 2 wherein at least one of said plastic sheets is transparent.

4. An assembly according to claim 2 wherein said sheets are elongated rectangular sheet and a pair of said continuous strips is positioned over and attached to both sides of the sheet.

5. An assembly according to claim 4 wherein the strips are heat-sealed to the sheets and the ends of the pouch are sealed by heat sealing.

6. An assembly according to claim 2 wherein the interior surface of one of said sheets has paper bonded thereto.

7. An assembly according to claim 2 wherein at least one of said sheets is porous to sterilizing vapors.

8. An assembly according to claim 1 wherein the interior surface of said first member has paper bonded thereto.

9. An assembly according to claim 1 wherein at least one of said sheet or said first member is porous to sterilizing vapors.

10. An assembly according to claim 1 wherein said means for initiating peel includes a score on the exterior of said sheet to facilitate opening of the sealed assembly.

11. An assembly according to claim 10 wherein a tab is positioned on the exterior of said scored sheet adjacent to the score.

* * * * *